United States Patent [19]
Tung et al.

[11] Patent Number: 5,155,082
[45] Date of Patent: Oct. 13, 1992

[54] CATALYST FOR THE MANUFACTURE OF CHLOROFLUOROCARBONS, HYDROCHLOROFLUOROCARBONS AND HYDROFLUOROCARBONS

[75] Inventors: Hsueh S. Tung, Williamsville; Addison M. Smith, Amherst, both of N.Y.

[73] Assignee: Allied-Signal Inc., Morristown, N.J.

[21] Appl. No.: 684,636

[22] Filed: Apr. 12, 1991

[51] Int. Cl.$^5$ .................. B01J 21/04; B01J 27/132
[52] U.S. Cl. .................. 502/228; 570/166; 570/168
[58] Field of Search .............. 502/228, 320; 570/166, 570/168

[56] References Cited

U.S. PATENT DOCUMENTS

| | | | |
|---|---|---|---|
| 2,991,255 | 7/1961 | Malley et al. | 502/320 |
| 3,717,586 | 2/1973 | Suggitt et al. | 502/320 X |
| 3,755,477 | 8/1973 | Firth et al. | 502/228 X |
| 3,778,388 | 12/1973 | Cornelius et al. | 502/320 |

*Primary Examiner*—W. J. Shine
*Attorney, Agent, or Firm*—Colleen D. Szuch; Jay P. Friedenson

[57] ABSTRACT

The invention relates to a novel catalyst and process for producing various chlorofluorocarbons, hydrochlorofluorocarbons and hydrofluorocarbons said catalyst prepared by co-extruding aluminum/chromium oxide and optionally impregnating the aluminum/chromium oxide support with a metal salt. The chlorofluorocarbons, hydrochlorofluorocarbons and hydrofluorocarbons, i.e., e.g., 1,1-dichloro-2,2,2-trifluoroethane, produced using the catalyst of the invention are useful in a variety of industrial applications including blowing agent, refrigerant, sterilant gas and solvent applications.

14 Claims, No Drawings

CATALYST FOR THE MANUFACTURE OF CHLOROFLUOROCARBONS, HYDROCHLOROFLUOROCARBONS AND HYDROFLUOROCARBONS

FIELD OF THE INVENTION

The invention relates to a novel catalyst and process for producing various chlorofluorocarbons, hydrochlorofluorocarbons and hydrofluorocarbons. The catalyst of the invention is prepared by co-extruding aluminum/chromium oxide and optionally impregnating the aluminum/chromium oxide support with a metal halide. The chlorofluorocarbons, hydrochlorofluorocarbons and hydrofluorocarbons produced using the catalyst of the invention are useful in a variety of industrial applications including blowing agent, refrigerant, sterilant gas and solvent applications.

BACKGROUND OF THE INVENTION

Although chlorofluorocarbons (CFCs), like trichlorofluoromethane (CFC-11), dichlorodifluoromethane (CFC-12), 1,1,2-trichloro-1,2,2-trifluoroethane (CFC-113) and chloropentafluoroethane (CFC-115) have a variety of industrial and household applications including refrigerant, solvent and blowing agent applications, they may be deleterious to the earth's protective ozone layer. Because of the potential destruction of atmospheric ozone by CFCs, there is a great need to develop substitutes for these compounds which function in substantially the same way as the CFCs but are low or zero ozone depleting. Several such replacement materials include 1,1-dichloro-2,2,2-trifluoroethane (HCFC-123), 1-chloro-1,2,2,2-tetrafluoroethane (HCFC-124), pentafluoroethane (HFC-125) and 1,1,1,2-tetrafluoroethane (HFC-134a). Because the demand for these and others low or zero ozone depleting materials will increase dramatically in the future, commercially viable processes for the preparation of these materials are needed.

Several methods for the production of hydrochlorofluorocarbons and hydrofluorocarbons are reported in the prior art. These methods, however, are not without their shortcomings. Many of these known processes utilize catalysts which are not very selective and, as a result, produce the desired hydrochlorofluorocarbons or hydrofluorocarbon along with a host of other by-products thus reducing the yield of the desired product. Some of these catalysts are hindered by their very short life span which makes them impractical for commercial production. The operating conditions described in the art also make many of the known processes for the production of hydrochlorofluorocarbons and hydrofluorocarbons impractical for commercial production. Among the prior art processes, the following are typical. Except where otherwise indicated, the term "combined 120's" as used herein shall refer to the combined selectivities of chlorofluorocarbons and/or hydrochlorofluorocarbons and/or hydrofluorocarbons produced in a given hydrofluorination reaction.

U.S. pat. No. 3,755,477 to Imperial Chemical Industries Ltd. describes a process for producing fluorinated aliphatic hydrocarbons which comprises fluorinating a halogenated hydrocarbon, including tetrachloroethylene, by reaction in the gas phase with HF in the presence of a steam-treated and calcined chromium oxide catalyst prepared by a multi-step process. The process of the invention as exemplified by Example 23 reports a selectivity for combined 120's of only 70% while producing a substantial amount of the less desired chloropentafluoroethane.

U.S. Pat. No. 3,258,500 to DuPont describes a process for the catalytic vapor phase reaction of HF with halohydrocarbons, including tetrachloroethylene, employing a catalyst that consists essentially of a heat-activated anhydrous chromium (III) oxide which may be supported on alumina. The reference also discloses that catalysts, in the form of activated chromium (III) oxide admixed with aluminum oxide may be used in the process of the invention. The catalyst is prepared by co-precipitation. Like the above-described process, this process exhibits a selectivity for combined 120's of only 73.7%. The remaining almost 26% was unaccounted for (and presumably was waste). See Example 17.

GB 1,000,485 to Scipioni et al., describes a process for the preparation of organic fluorinated compounds by fluorination of halo-olefins in the gaseous phase. The catalyst consists essentially of partially fluorinated alumina impregnated with one or more polyvalent metal halides. The polyvalent metal may be chromium, cobalt, nickel or manganese. The total content of polyvalent metal halide, expressed as oxide, is not more than 15% by weight of the partially fluorinated (70-80%) alumina. Example 4 (Table 4) shows that reaction of tetrachloroethylene with HF over said catalyst yields dichlorotrifluoroethane as the major product. The patent also provides that if fluorination of the catalyst is excessive, the activity of the catalyst is impaired.

U.S. Pat. No. 4,843,181 to DuPont describes a gas-phase process for the manufacture of 1,1,1-trifluorodichloroethane and/or 1,1,1,2-tetrafluoroethane by contacting a suitable tetrahaloethylene, including tetrachloroethylene, and/or pentahaloethane with HF in the presence of $Cr_2O_3$ prepared by pyrolysis of $(NH_4)_2Cr_2O_7$. In order to obtain the desired product in high yield, this process requires a long contact time (i.e., 90 seconds) between the catalyst and reactants making the process impractical for commercial operation.

U.S. Pat. No. 4,967,023 to Ausimont discloses a process for preparing 1,1,1-trifluoro-2,2-dichloroethane by hydrofluorination, in the gas phase, of perchloroethylene in the presence of a catalyst comprising chromium oxide supported on $AlF_3$ in the gamma and/or beta form. This process suffers from low conversion of the reactants resulting in low productivity of 1,1,1-trifluoro-2,2-dichloroethane.

Kokai Patent Publication No. 178237 Published Jul. 11, 1990, discloses a method of making 1,1,2-trichloro-2,2-difluoroethane, 1,1-dichloro-2,2,2-trifluoroethane, 1-chloro-1,2,2,2-tetrafluoroethane and pentafluoroethane by fluorinating perchloroethylene in the gas phase with HF in the presence of a fluorination catalyst which consists of an oxide containing Cr and at least one element selected from the group of Al, Mg, Ca, Ba, Sr, Fe, Ni, Co and Mn. The catalyst is prepared by co-precipitation.

It is a particular object of the invention to provide a catalyst which is useful in the production of chlorofluorocarbons, hydrochlorofluorocarbons and hydrofluorocarbons.

It is another object of the invention to provide a catalyst with a high productivity.

It is another object of the invention to provide a catalyst which is highly active.

It is another object of the invention to provide a catalyst which has a long life.

Still another object of the invention is to provide a catalyst which can be easily regenerated.

Other objects and advantages of the invention will become apparant from the following description.

SUMMARY OF THE INVENTION

The invention relates to a novel catalyst and process for preparing a desired chlorofluorocarbon, hydrochlorofluorocarbon or hydrofluorocarbon said catalyst comprising a mixture of aluminum and chromium oxide and optionally a metal salt and prepared by the coextrusion of aluminum oxide hydroxide with chromium oxide and optionally impregnation with a metal salt.

The chlorofluorocarbons, hydrochlorofluorocarbons and hydrofluorocarbons produced by this process may be used in a variety of industrial applications including solvent, refrigerant, sterilant gas and blowing agent applications.

DETAILED DESCRIPTION OF THE INVENTION

The invention relates to a novel catalyst and process for the hydrofluorination of a halogenated aliphatic hydrocarbon to produce a chlorofluorocarbon, hydrochlorofluorocarbon or hydrofluorocarbon. A key feature of the invention is that through catalyst selection and preparation, the desired product, can be obtained as the major product at high productivity, normally greater than 10 lbs/hr/ft$^3$. In addition, because of the catalyst's high selectivity, only small amounts of non-recyclable by-products are formed (i.e., usually less than 5%).

The catalyst of the invention is prepared by the coextrusion of aluminum oxide hydroxide and chromium oxide and optionally the impregnation of a metal salt followed by calcination at high temperature in air. Specifically, the aluminum oxide hydroxide and chromium oxide particles are kneaded into a thick paste in a solvent such as water, alcohol or dilute mineral acid. Dilute nitric acid (i.e., about 6 wt. % solution) and water are preferred. The amount of solvent used is not critical. Preferably, the amount of solvent should be adjusted so that the extrudate has a mimimum crush strength of greater than about 2 lbs. Crush strength may be determined using any of the techniques well known in the art. It may be determined, for example, using the Flat Plate Side Crush Strength Method.

The mixture is then extruded and preferably calcined. The conditions for extrusion, including temperature, pressure, the size of the extruder, the die size and extrusion rate are not critical. For example, the extruder may be General Electrics's Brabender Model 100, the die may be a 1/16 inch single hole die, the rate of extrusion may be from about 2 to about 10 lbs/hr and the extrusion may be conducted at room temperature and zero pressure.

Optionally, the aluminum/chromium oxide support may be impregnated with a metal salt. If this is done, then Prior to impregnation, the extruded aluminum/chromium oxide support is calcined. Metal salts useful in the invention include metal halides such as cobalt, nickel, manganese, rhodium and ruthenium halide. Chlorine is the preferred halide. Following impregnation, the catalyst is dried and may be calcined.

The chromium (III) oxide may be crystalline chromium oxide or amorphous chromium oxide having a preferred median particle size of less than 100 microns, more preferably less than 70 microns and most preferably, less than 50 microns.

The aluminum oxide hydroxide preferably has a median particle size of less than 100 microns, more preferably, less than 50 microns and most preferably less than 30 microns.

Chromium (III) oxide and aluminum oxide hydroxide are commercially available materials which may be Purchased in a variety of particle sizes. Chromium (III) oxide may be purchased, for example, from Great Western Inorganics of Golden, Colorado while aluminum oxide hydroxide is available, for example, through Vista Chemical Inc.

The preferred mole ratio of aluminum:chromium oxide is from about 95:5 to about 5:95, more preferably from about 85:15 to about 40:60 and most preferably from about 80:20 to about 50:50. When a metal salt is used, the preferred loading of the metal salt is from about 0.1 to about 20 wt. % of the mixed oxide support, more preferably from about 0.3 to about 10 wt. % of the mixed oxide support and most Preferably from about 0.5 to about 5 wt. % of the mixed oxide support.

Impregnation of the mixed oxide support with a metal salt may be accomplished by any means well known in the art. For example, impregnation may be accomplished in accordance with step (b) of Example 1 discussed below.

Calcination conditions after extrusion are important to catalyst activity. Calcination can be conducted in an uncontrolled atmosphere of stagnant air or in a controlled continuous flow of air or inert atmosphere. Preferably calcination is accomplished at a temperature of from about 200° to about 800° C., more preferably from about 300° to about 600° C. and most preferably from about 350° to about 500° C. resulting in a catalyst with a high surface area.

Preferably, the resulting product is pretreated with HF before use. It is thought that this converts some of the surface aluminum oxide to aluminum fluoride and/or aluminum oxy-fluoride and converts some of the surface chromium oxide to chromium oxy-fluoride. This pretreatment can be accomplished by passing an excess of HF over the catalyst at an initial temperature of 200° C. The exotherm generated by this step may be controlled by using air or an inert gas as diluent for the HF. After the exotherm disappears, pure HF can be used. At this point, the temperature is raised to at least about 300° C. and the catalyst is maintained at this temperature for from about 2 to about 8 hours.

The catalyst of the invention has a life of more than 1800 hours with periodic regeneration. Catalyst activity or catalyst life can be maintained without regeneration by cofeeding air or oxygen to the reactor. The amount of air or oxygen supplied to the reactor is preferably controlled at from about 0.01 to about 30 mole % of oxygen or air relative to the total organics fed to the reactor, more preferably from about 0.05 to about 20 mole % and most preferably from about 0.1 to about 10 mole %. Otherwise, periodic regeneration may be easily accomplished, for example, by repeating the procedure described in Example 1(c) below.

Generally, the process embodiment of the invention is as follows.

In a process for preparing a desired chlorofluorocarbon, hydrochlorofluorocarbon or hydrofluorocarbon wherein a halogenated aliphatic hydrocarbon is reacted with anhydrous hydrogen fluoride in the presence of a catalyst comprising a mixture of partially fluorinated aluminum and chromium oxide and optionally a metal salt, the improvement comprises:

(a.) preparing said catalyst by blending aluminum oxide hydroxide and chromium oxide together in the presence of a solvent, extruding the blend and optionally impregnating the blend with a metal salt.

The degree to which the catalyst is fluorinated is not critical. Significant catalytic activity results when the catalyst is at least 5% fluorinated and Preferably not more than 90% fluorinated. Fluorination in excess of 90% may result in catalyst deactivation.

Preferably, the halogenated aliphatic hydrocarbon contains between two and six carbon atoms and more preferably contains between two and three carbon atoms.

Most preferably, the halogenated hydrocarbon is selected from the group consisting of $C_2H_xCl_{4-x-y}F_y$, wherein $x=0$ to 1 and $y=0$ to 3, $C_2H_xCl_{6-x-y}F_y$, wherein $x=0$ to 2 and $y=0$ to 4 and mixtures thereof and includes trihaloethylenes like trichloroethylene, tetrahaloethylenes such as perchloroethylene, 1-fluoro-1,2,2-trichloroethylene, 1,1-difluoro-2,2-dichloroethylene and 1,1,2-trifluoro-2-chloroethylene, tetrahaloethanes like 1-chloro-2,2,2-trifluoroethane, pentahaloethanes such as 1,1-dichloro2,2,2-trifluoroethane, 1,2-dichloro-1,2,2-trifluoroethane, 1-chloro-1,2,2,2-tetrafluoroethane, 1-chloro-1,1,2,2-tetrafluoroethane, pentachloroethane, 1,1,2,2-tetrachloro-1-fluoroethane, 1,1,1,2-tetrachloro-2-fluoroethane, 1,1-difluoro1,2,2-trichloroethane and 1,2-difluoro-1,1,2-trichloroethane and hexahaloethanes such as 1,1,1-trichloro-2,2,2-trifluoroethane and mixtures thereof.

When 1,1-dichloro-2,2,2-trifluoroethane is the desired hydrochlorofluorocarbon, the preferred starting material is perchloroethylene. When 1-chloro-1,2,2,2-tetrafluoroethane (HCFC-124) is the desired hydrochlorofluorocarbon, the preferred starting material is 1,1-dichloro-2,2,2-trifluoroethane (HCFC-123) or 1,2-dichloro-1,2,2-trifluoroethane (HCFC-123a). When pentafluoroethane (HFC-125) is the desired hydrofluorocarbon, the preferred starting material is HCFC-123, or HCFC-123a or HCFC-124. When 1,1-dichloro-1,2,2,2-tetrafluoroethane (CFC-114a) is the desired chlorofluorocarbon, the preferred starting material is 1,1,1-trichloro-2,2,2-trifluoroethane (CFC-113a). When 1,1,1,2-tetrafluoroethane (HFC-134a) is the desired hydrofluorocarbon, the preferred starting material is 1-chloro-2,2,2-trifluoroethane (HCFC-133a). When the desired hydrochlorofluorocarbon is HCFC-133a, trichloroethylene is the Preferred starting material.

The temperature at which the fluorination reaction is conducted can range, for example, from about 200° to about 450° C., preferably from about 250° to about 400° C. and most preferably from about 290° to about 350° C. with a contact time, of for example, about 2 to about 120 seconds, preferably about 5 to about 80 seconds, more preferably about 8 to about 60 seconds and most preferably about 10 to about 50 seconds. For purposes of this invention, contact time shall be the time required for the gaseous reactants to pass through the catalyst bed assuming that the catalyst bed is 100% void.

The molar ratio of HF to organics (saturated or unsaturated halogenated aliphatic hydrocarbon) can range for example, from about 3:1 to about 12:1, more preferably about 4:1 to about 10:1 and most preferably about 4:1 to about 8:1.

Pressure is not critical. Atmospheric and superatmospheric pressures are the most convenient and are therefore preferred. In Particular, high reaction pressure is desirable for product recovery purposes.

The saturated or unsaturated halogenated aliphatic hydrocarbons, hydrogen fluoride, aluminum oxide hydroxide, chromium oxide and metal salt components of the invention are known materials. Preferably, they should be used in high purity so as to avoid the introduction of adverse influences upon the reaction system.

The fluorination reaction may be conducted in any suitable reaction vessel. The reaction vessel should be constructed from materials which are resistant to the corrosive effects of HF such as HASTELLOY, INCONEL and MONEL.

When the desired hydrochlorofluorocarbon is HCFC-123 and the starting material is perchloroethylene, the by-products produced include HCFC-123a, HCFC-124, HCFC-124a, 1,1,2-trichloro-2,2-difluoroethane, fluorotrichloroethylene, fluorotetrachloroethane, HCFC-133a and perhalogenated ethane When the desired hydrochlorofluorocarbon is HCFC-124 and the starting material is a mixture of HCFC-123 and HCFC-123a, the by-products produced include HCFC-124a, HFC-125 and perhalogenated compounds.

When the desired hydrofluorocarbon is HFC-125 and the starting material is a mixture of HCFC-123 and HCFC-123a, the by-products which are produced include HCFC-124 and HCFC-124a.

When the desired chlorofluorocarbon is CFC-114a and the starting material is CFC-113a, the by-products which are produced include chloropentafluoroethane.

When the desired hydrofluorocarbon is HFC-134a and the starting material is HCFC-133a, the by-Products which are produced include HCFC-123, HCFC-124 and tetrafluoroethane.

When the desired hydrofluorocarbon is HCFC-133a and the starting material is trichloroethylene, the by-products which are produced include HFC-134a, HCFC-123 and HCFC-124.

Many of the by-products formed during the course of each of the fluorination reactions (i.e., e.g., 1,1,2-trichloro-2,2-difluoroethane (HCFC-122), fluorotrichloroethylene and fluorotetrachloroethane in the case of HCFC-123 and HCFC-124 and HCFC-124a in the case of HFC-125) can be recycled to the reaction vessel for the production of additional HCFC-123, HCFC-124, HFC-125, CFC-114a, HFC-134a and HCFC-133a respectively.

The present invention is more fully illustrated by the following non-limiting examples.

EXAMPLE 1

(a) Catalyst Preparation - - - aluminum/chromium oxide co-extrudate

Ground chromium oxide powder with a median particle size of about 37 microns was mixed with aluminum oxide hydroxide powder with a medium particle size of less than about 0.2 microns. The mole ratio of aluminum:chromium was about 70:30 wt. %. Six weight percent (6 wt %) nitric acid was added to the mixed oxides and the mixture was kneaded to form a thick paste. The paste was then charged to a BRABENDER and extruded using a 1/16 inch single hole die. The extrudate was dried in an oven overnight at 82°–90° C. and was then calcined in a muffle furnace at about 490° C. for 2–3 hours. After cooling, the extrudate was sized to an approximate L/D (length/diameter) of 3. The surface area of the extrudate was 229 m²/g.

(b) Catalyst Preparation - - - impregnation of metal salt 245 g of aluminum/chromium oxide extrudate were placed in about 260 ml of 0.24M CoCl₂ solution for approximately 16-20 hours. The wet extrudate was filtered and dried in a vacuum oven at about 100°-110° C. for 2.5 days The CoCl₂ loading was 1.4 wt. %.

(c) Calcination and HF Pretreatment

The catalyst is calcined and subsequently treated with HF prior to being used in the fluorination of organics. Approximately 100-110 ml of catalyst were packed into a ½ inch MONEL reactor. A steady stream of air at about 2-3 liters/min. flowed through the catalyst bed. The temperature of the reactor was raised rapidly to 400° C. and held at this temperature for 16 hours. Then, the temperature was lowered to 200° C. and air was replaced with nitrogen at about 0.5-1.5 liters/min. HF was pumped in the reactor at about 1-2 ml/min. After the exotherm disappeared, the nitrogen was turned off and the temperature was raised to 400° C. and held for 8 hours.

EXAMPLES 2-5

Preparation of HCFC-123 using the catalyst of Example 1(a)

In this set of examples, the catalyst prepared in Example 1(a), after calcination and pretreatment with with HF, (in accordance with the procedures in Example 1(c)) was used for the fluorination of perchloroethylene. After the catalyst was calcined and pretreated with HF, the reactor temperature was lowered to the desired reaction temperature for fluorination of perchloroethylene. Perchloroethylene was pumped into the reactor and the HF:organics ratio was adjusted to about 8. The reaction was conducted at 200 psig pressure. The reaction conditions and results of the experiments are reported in Table I below. The effluent of the reactor was analyzed using an on-line gas chromatograph.

TABLE 1

| | EXAMPLES | | | |
|---|---|---|---|---|
| | 2 | 3 | 4 | 5 |
| Feed: | Perchloroethylene | | | |
| Catalyst: | Al₂O₃/Cr₂O₃ | | | |
| Pressure psig: | 200 | 200 | 200 | 200 |
| Mole Ratio (HF/PCE): | 8 | 8 | 8 | 8 |
| Temperature (°C.): | 300 | 310 | 320 | 330 |
| Contact Time[1] (seconds): | 38 | 38 | 36 | 26 |
| Conversion PCE (%): | 42 | 57 | 68 | 60 |
| Selectivity (%): | | | | |
| HCFC-125 | 0.1 | 0.2 | 0.5 | 0.4 |
| HCFC-124 & 124a | 1.0 | 5.6 | 11.2 | 10.3 |
| HCFC-123 & 123a | 30.8 | 48.9 | 60.2 | 56.9 |
| Recyclable By-Products: | 66.3 | 43.8 | 25.4 | 28.5 |
| Non-recyclable By-products: | 1.1 | 1.1 | 2.3 | 3.4 |
| Combined 120's[2] | 98.2 | 98.5 | 97.3 | 96.1 |
| Productivity (lbs/hr/ft³): 123 & 123a | 4.0 | 8.7 | 12.8 | 15.9 |

[1]Contact time = the time required for the gaseous reactants to pass through the catalyst bed assuming the catalyst bed is 100% void.
[2]Includes selectivities of HFC-125, HCFC-124, HCFC-124a, HCFC-123, HCFC-123a and recyclable by-products.

Hydrofluorination of perchloroethylene produced not only HCFC-123 and 124, but also their respective isomers i.e., HCFC-123a and 124a. The amounts of isomers produced depended on the reaction conditions.

Because HCFC-123a can be isomerized to HCFC-123, the productivity of the process was expressed in pounds of HCFC-123 and 123a per hour per cubic foot of catalyst.

The productivity and selectivity of a catalyst to produce a desired product, in the instant case 1,1-dichloro-2,2,2-trifluoroethane, are the most important parameters to consider in evaluating catalyst performance. Selectivity measures the degree to which the catalyst will produce the desired product to the exclusion of other products while a catalysts' productivity measures the rate at which the catalyst can produce the desired product. Because productivity measures the rate at which a desired product can be Produced for a given amount of catalyst, it is a useful parameter for comparing the performance of different catalysts.

For Examples 2-4, the operating conditions, including contact time, were held essentially constant while the temperature was varied. Generally, the higher the temperature, the shorter the catalyst life. Therefore, it is desirable to use the lowest temperature possible while manitaining a high productivity. A comparison of Examples 2 and 3 reveals that for a 10° increase in temperature, the selectivity of combined 120's remains essentially constant while the productivity of HCFC-123 and HCFC-123a increases by 100%. A comparison of Examples 3 and 4 shows that once again, for a 10° increase in temperature, while the selectivity of combined 120's decreases slightly (i.e., about 0.8%), the productivity increases significantly (i.e., another 50%).

Normally, for commercial production it is desirable to have a productivity which is as high as possible without sacrificing selectivity and catalyst life. Therefore, based on a comparison of Examples 2-4, we conclude that the most desirable operating conditions for the aluminum/chromium oxide catalyst of the invention would be those described in Example 4.

Example 5 shows that productivity can be increased by increasing temperature and decreasing contact time with little effect on the selectivity of combined 120's. Note, once again, that elevated temperature reduces catalyst life.

EXAMPLES 6-9

Preparation of HCFC-123 using the catalyst of Example 1(b)

After calcination and treatment with HF in accordance with the procedures outlined in Example 1(c). the catalyst prepared in Example 1(b) was used for the fluorination of a mixture of 1,1,2-trichloro-2,2-difluoroethane (HCFC-122) and Perchloroethylene. As indicated above, some of the by-products of the reaction, like HCFC-122, are recyclable. Thus, this experiment not only reports on catalyst activity but also simulates by-product recycling. The reaction conditions and results are reported in Table II below.

TABLE 2

| | EXAMPLES | | | |
|---|---|---|---|---|
| | 6 | 7 | 8 | 9 |
| Catalyst: | CoCl$_2$/Al$_2$O$_3$/Cr$_2$O$_3$ | | | |
| Feed: | HCFC-122/PCE(29.63/70.37 wt %) | | | |
| Pressure Psig: | 200 | 200 | 200 | 200 |
| Mole Ratio (HF/Org.): | 8 | 8 | 8 | 8 |
| Contact Time[1] (seconds): | 38 | 38 | 36 | 36 |
| Temperature (°C.): | 290 | 310 | 320 | 330 |
| Conversion 122 + PCE (%): | — | 48 | 62 | 73 |
| Conversion PCE (%) | 39 | 65 | 70 | 75 |
| Conversion 122 (%): | — | 7 | 43 | 67 |
| Selectivity (%): | | | | |
| HFC-125 | 0.3 | 0.3 | 0.3 | 0.4 |
| HCFC 124 & 124a | 1.9 | 6.4 | 11.4 | 18.7 |
| HCFC-123 & 123a | 45.4 | 78.7 | 75.3 | 69.1 |
| Recyclable By-products: | 46.7 | 6.2 | 4.0 | 2.7 |
| Non-recyclable By-products: | 5.9 | 8.5 | 8.9 | 9.2 |
| Combined 120's[2]: | 94.3 | 91.6 | 91.0 | 90.9 |
| Productivity (lbs/hr/ft$^3$): | | | | |
| 123 & 123a | 3.9 | 11.8 | 14.6 | 15.7 |

[1] Contact time = the time required for the gaseous reactants to pass through the catalyst bed, assuming the catalyst bed is 100% void.
[2] Includes selectivities of HFC-125, HCFC-124, HCFC-124a, HCFC-123, HCFC-123a and recyclable by-products.

Once again, in this set of Examples, operating conditions, including contact time, were held essentially constant while temperature was varied, a comparison of the selectivities and productivities for these Examples indicates that Example 8 provides the best operating conditions for the aluminum/chromium oxide/cobalt chloride catalyst of the invention resulting in a selectivity and productivity which are highly desirable for commercial production.

COMPARATIVE EXAMPLES 1-2

In this next set of Examples, the activities of three aluminum/chromimum oxide (Al$_2$O$_3$/Cr$_2$O$_3$) catalysts having the same composition (70/30 mol ratio), but prepared by three different methods (i.e. co-extrusion, co-precipitation and agglomerization) were compared. Each catalyst is compared under those conditions which optimize its performance. A detailed description of the method of preparation and results of the comparison are reported below.

Co-extrusion

The catalyst of applicants' Example 4 is used for comparison.

Co-precipitation

This catalyst was prepared in accordance with the method outlined in U.S. Pat. No. 3,258,500 and U.S. Pat. No. 2,402,854. Aluminum hydroxide salt was precipitated with chromium hydroxide salt to give a 70/30 alumina/chromia mixture, (the same mole ratio as used in applicants' Examples 2-9). The catalyst was then calcined and treated with HF in accordance with the method described in applicants' Example 1(c) and subsequently used in the process described in applicants' Examples 2-5. Reaction temperatures were scanned from about 300° to about 400° C.

Agglomerization

A mixture of gamma alumina and chromium chloride hydroxide solution were poured into mineral oil to form spheres. The alumina/chromia spheres were then washed and calcined in air at 500° C. for about 2 hours. Before fluorination, the catalyst was again calcined and treated with HF in accordance with the method described in Example 1(c). The catalyst was then used in the process described in Examples 2-5. Reaction temperatures were scanned from about 300° to about 400° C.

For each of the catalysts, perchloroethylene conversion at different temperatures was plotted. See, attached FIG. 1. From this plot, one can determine and compare the activity of various catalysts (i.e., the higher the percent conversion at a given temperature, the more active the catalyst or, put another way, the higher the temperature needed to achieve a given conversion, the less active the catalyst). FIG. 1 shows that in order to achieve a 40% conversion using the catalyst of the invention, a temperature of only about 300° C. is necessary. This is contrasted with the catalysts prepared by co-precipitation and agglomerization which require a temperature of about 330° C. and about 390° C. respectively to achieve the same conversion.

As stated above, generally, catalyst life is dependent on reaction temperature, i.e,. the lower the reaction temperature, the longer the catalyst will last. Based on the data from FIG. 1, it is apparent that the catalyst of our invention is significantly more active than the catalysts prepared by co-precipitation and agglomerization and, since it may be used at lower temperatures, one would expect it to have a much longer catalyst life.

In summary, one can clearly conclude that catalyst activity is very much dependent on the method used to prepare the catalyst and not just on catalyst composition. The Al$_2$O$_3$/Cr$_2$O$_3$ catalyst of the present invention, prepared by co-extrusion is surprisingly more active than other Al$_2$O$_3$/Cr$_2$O$_3$ catalysts prepared by co-precipitation and agglomerization and has a much longer catalyst life.

TABLE 3

| | Co-Ex. | Agglomerate | Co-Ppt. |
|---|---|---|---|
| Mole Ratio (HF/PCE): | 8 | 8 | 8 |
| Temp. (°C.): | 320 | 375 | 375 |
| PCE Conversion (%): | 68 | 68 | 35 |
| Selectivities: | | | |
| Comb. 120's[1]: | 97 | 90 | 92 |
| Productivity (lbs/hr/ft3): | | | |
| HCFC-123/123a: | 13 | 12 | 5 |

[1] Includes selectivities of HFC-125, HCFC-124, HCFC-124a, HCFC-123, HCFC-123a and recyclable by-products.

In addition to being significantly more active and having a longer catalyst life than the other catalysts, the data in Table 3 show that the catalyst of the invention is surprisingly significantly more selective for combined 120's and results in a higher productivity than the catalysts prepared by co-precipitation and agglomerization.

EXAMPLES 10-15

Preparation of HCFC-124 using the catalyst of Example 1(a)

After the catalyst was calcined and pretreated with HF in accordance with Example 1(c), the reactor temperature was lowered to the desired reaction temperature for fluorination of HCFC-123 which contained 21.6% HCFC-123a. The HCFC-123 was pumped into the reactor and the HF:organics ratio was adjusted to about 5. The reaction was conducted at 200 psig pressure. The effluents of the reactor were analyzed using an on-line gas chromatograph. The reaction conditions and results of the experiments are reported in Table 4 below.

TABLE 4

| | EXAMPLES | | | | | |
|---|---|---|---|---|---|---|
| | 10 | 11 | 12 | 13 | 14 | 15 |
| Catalyst: | $Al_2O_3/Cr_2O_3$ | | | | | |
| Feed: | HCFC-123 with 21.6% HCFC-123a | | | | | |
| Pressure: Psig | 200 | 200 | 200 | 200 | 200 | 200 |
| Mole Ratio (HF/123): | 5 | 5 | 5 | 5 | 5 | 5 |
| Contact Time[1] (seconds): | 48 | 34 | 34 | 33 | 28 | 46 |
| Temperature (°C.): | 330 | 330 | 340 | 350 | 350 | 350 |
| Conversion 123 (%): | 51 | 34 | 55 | 64 | 57 | 75 |
| Selectivity (%): | | | | | | |
| HCFC-125: | 6.3 | 3.5 | 8.3 | 11.0 | 9.4 | 24.2 |
| HCFC-124 & 124a: | 92.6 | 94.5 | 90.9 | 88.4 | 89.7 | 75.2 |
| Combined 120's[2]: | 98.9 | 98.0 | 99.2 | 99.4 | 99.1 | 99.4 |
| Non-recyclable By-products: | 0.6 | 0.8 | 0.5 | 0.5 | 0.4 | 0.4 |
| Productivity (lbs/hr/ft$^3$): | | | | | | |
| 125: | 0.9 | 0.4 | 1.5 | 2.3 | 2.2 | 4.9 |
| 124 & 124a: | 14.2 | 11.8 | 18.1 | 20.7 | 23.6 | 17.1 |

[1]Contact time = the time required for the gaseous reactants to pass through the catalyst bed assuming the catalyst bed is 100% void.
[2]Includes selectivities of HFC-125, HCFC-124 and HCFC-124a.

For Examples 11-13, the operating conditions, including contact time, were held essentially constant while the temperature was varied. A comparison of Examples 11 and 12 reveals that for a 10° increase in temperature, the selectivity of combined 120's stays essentially the same while the productivity of HCFC-124 and HCFC-124a increases by about 50%. A comparison of Examples 12 and 13 indicates that, once again, for a 10° increase in temperature, the selectivity of the combined 120's is virtually unchanged while the productivity of HCFC-124 and HCFC-124a increased by only about 14%. Based upon the above comparasion, we conclude that the most desirable operating conditions for the catalyst would be those described in Example 12 since the productivity remains high without sacrificing selectivity and catalyst life (i.e., the lower the temperature the longer the catalyst life).

In Examples 13-15, the operating conditions, including temperature, were held essentially constant while the contact time was varied. These Examples show that as the contact time increases, the selectivity and productivity of HFC-125 increases while the selectivity and Productivity of HCFC-124 and HCFC-124a decreases.

EXAMPLES 16-19

Preparation of HCFC-124 using the catalyst of Example 1(b)

The catalyst prepared in Example 1(b) was calcined and treated with HF in accordance with Example 1(c) above. The catalyst was then used for the fluorination of HCFC-123. The results and reaction conditions are reported in Table 5 below.

TABLE 5

| | EXAMPLES | | | |
|---|---|---|---|---|
| | 16 | 17 | 18 | 19 |
| Catalyst: | $CoCl_2/Al_2O_3/Cr_2O_3$ | | | |
| Feed: | HCFC-123 with 4% HCFC-123a | | | |
| Pressure psig: | 200 | 200 | 200 | 200 |
| Mole Ratio (HF/123): | 4 | 4 | 4 | 4 |
| Contact Time[1] (seconds): | 45 | 44 | 43 | 42 |
| Temperature (°C.): | 310 | 330 | 340 | 350 |
| Conversion 123 (%): | 11 | 35 | 48 | 59 |
| Selectivity (%): | | | | |
| HCFC-125: | 1.0 | 7.3 | 9.7 | 15 |
| HCFC-124 & 124a: | 98.6 | 90.5 | 88.8 | 83.4 |
| Combined 120's[2]: | 99.6 | 97.8 | 98.5 | 98.4 |
| Non-recyclable By-products: | 0.4 | 2.1 | 1.5 | 1.3 |
| Productivity (lbs/hr/ft$^3$): | | | | |
| 125: | 0.03 | 1.0 | 1.8 | 3.4 |
| 124 & 124a: | 4.6 | 14.2 | 18.0 | 21.1 |

[1]Contact time = the time required for the gaseous reactants to pass through the catalyst bed assuming the catalyst bed is 100% void.
[2]Includes selectivities of HFC-125, HCFC-124, HCFC-124a.

In Examples 16-19, the operating conditions, including contact time were held essentially constant while temperature was varied. A comparison of Examples 16 and 17 reveals that for a 20° increase in temperature the selectivity of combined 120's decreases slightly while the productivity of HCFC-124 and HCFC-124a increases by about 208%. A comparison of Examples 17 and 18 shows that for a 10° increase in temperature the selectivity of combined 120's stays essentially the same while the productivity of HCFC-124 and HCFC-124a increases by about 28%. Finally, a comparison of Examples 18 and 19 shows that for a 10° increase in temperature the selectivity of combined 120's is unchanged while the productivity increases by about 17%.

Based on the above comparison, we conclude that the optimum operating conditions for the catalyst are those described in Example 17.

EXAMPLE 20

Preparation of HFC-125 using the catalyst of Example 1(a)

The catalyst prepared in Example 1(a) is calcined and treated with HF in accordance with the procedure outlined in Example 1(c) above. This catalyst is then used for the fluorination of HCFC-123. The results indicate that the catalyst of the invention is highly selective for HFC-125 and results in a productivity for HFC-125 which is highly desirable for commercial production.

EXAMPLE 21

Preparation of HFC-125 using the catalyst of Example 1 (b)

The catalyst prepared in Example 1(b) is calcined and treated with HF in accordance with the procedure outlined in Example 1(c) above. The catalyst is then used for the fluorination of HCFC-123. The results indicate that the catalyst of the invention is highly selective for HFC-125 and results in a productivity for HFC-125 which is highly desirable for commercial production.

EXAMPLES 22-24

Preparation of CFC-114a using the catalyst of Example 1(a)

The catalyst prepared in Example 1(a) was calcined and treated with HF in accordance with the procedure outlined in Example 1(c) above. This catalyst was then used for the fluorination of CFC-113a. The results and reaction conditions are reported in Table 6 below.

TABLE 6

| | EXAMPLES | | |
|---|---|---|---|
| | 22 | 23 | 24 |
| Catalyst: | $Al_2O_3/Cr_2O_3$ | | |
| Feed: | CFC-113a | | |
| Pressure Psig: | 200 | 200 | 200 |
| Mole Ratio (HF/113a): | 4.9 | 4.9 | 4.9 |
| Contact Time[1] (seconds): | 46 | 46 | 47 |
| Temperature (°C.): | 300 | 310 | 320 |
| Conversion 113a (%): | 81 | 94 | 97 |
| Selectivity (%): | | | |
| HCFC-115: | 1.0 | 7.3 | 9.7 |
| HCFC-114a: | 98.6 | 90.5 | 88.8 |
| HCFC-124 & HCFC-133a: | 0.8 | 1.0 | 1.3 |
| Productivity (lbs/hr/ft$^3$): | | | |
| 114a: | 32 | 38 | 38 |

[1]Contact time = the time required for the gaseous reactants to pass through the catalyst bed assuming the catalyst bed is 100% void.

For Examples 22-24, the operating conditions, including contact time were held essentially constant while the temperature was varied. A comparison of Examples 22 and 23 reveals that for a 10° increase in temperature, the selectivity for HCFC-114a remained unchanged while the productivity increased 19%. A comparison of Examples 23 and 24 shows that for a 10° increase in temperature the selectivity for HCFC-114a and productivity remain essentially the same. Thus, it appears that the conditions outlined in Example 23 provide the optimum operating conditions for the catalyst.

EXAMPLE 25

Preparation of CFC-114a using the catalyst of in Example 1(b)

The catalyst prepared in Example 1(b) is calcined and treated with HF in accordance with Example 1(c) above. The catalyst is then used for the fluorination of CFC-113a. The results indicate that the catalyst of the invention is highly selective for CFC-114a and results in a productivity for CFC-114a which is highly desirable for commercial production.

EXAMPLE 26

Preparation of HCFC-133a using the catalyst of Example 1(a)

The catalyst prepared in Example 1(a) is calcined and treated with HF in accordance with the procedure outlined in Example 1(c) above. This catalyst is then used for the fluorination of trichloroethylene. The results indicate that the catalyst of the invention is highly selective for HCFC-133a and results in a productivity for HCFC-133a which is highly desirable for commercial production.

EXAMPLE 27

Preparation of HCFC-133a using the catalyst of Example 1(b)

The catalyst prepared in example 1(b) is calcined and treated with HF in accordance with Example 1(c) above. The catalyst is then used for the fluorination of trichloroethylene. The results indicate that the catalyst of the invention is highly selective for HCFC-133a and results in a productivity for HCFC-133a which is highly desirable for commercial production.

EXAMPLE 28

Preparation of HFC-134a using a catalyst prepared according to the procedure set forth in Example 1(a)

A catalyst having the composition of 30 mol % aluminum and 70 mol % chromium oxide was prepared according to the procedures set forth in Example 1(a). The catalyst was then calcined and treated with HF in accordance with the procedure outlined in Example 1(c) above and subsequently used for the fluorination of HCFC-133a. Air was cofed to the reactor with HF and HCFC-133a to maintain catalyst activity. The results and reaction conditions are reported in Table 7 below.

TABLE 7

| | EXAMPLE 25 |
|---|---|
| Catalyst: | $Al_2O_3/Cr_2O_3$ (30/70) |
| Feed: | HCFC-133a |
| Pressure Psig | 45 |
| Mole Ratio (HF/133a): | 4.1 |
| Air Cofeed ($O_2$/133a)[1]: | 2 |
| Contact Time[2] (seconds): | 12 |
| Temperature (°C.): | 350 |
| Conversion 133a (%): | 18 |
| Selectivity (%): | |
| HFC-134a: | 94 |
| HCFC-143a: | 0.3 |
| HCFC-124: | 1.8 |
| HCFC-1122: | 0.2 |
| HCFC-123: | 3.3 |
| Productivity (lbs/hr/ft$^3$): | |
| 134a: | 5.0 |

[1](mole %)
[2]Contact time = the time required for the gaseous reactants to pass through the catalyst bed assuming the catalyst bed is 100% void.

The results shown in Table 6 indicate that the catalyst is highly selective for HFC-134a. This reaction was run for more than 800 hours and the catalyst showed no sign of deactivation.

What is claimed:

1. An aluminum/chromium oxide catalyst prepared by:
   (a) blending aluminum oxide hydroxide and chromium oxide together in the presence of a solvent;
   (b) extruding the blend;
   (c) calcining the blend; and
   (d) partially fluorinating the blend.

2. The catalyst of claim 1 wherein step (d) is accomplished by pretreating said catalyst before use with hydrogen fluoride.

3. The catalyst of claim 1 wherein said aluminum oxide hydroxide and chromium oxide have a median particle size of less than 100 microns.

4. The catalyst of claim 1 wherein said aluminum oxide hydroxide and chromium oxide have a median particle size of less than 50 microns.

5. The catalyst of claim 1 wherein said aluminum oxide hydroxide and chromium oxide have a particle size of less than 30 microns.

6. The catalyst of claim 1 wherein the mole ratio of aluminum to chromium oxide is about 95:5 to about 5:95.

7. The catalyst of claim 1 wherein following extrusion the catalyst is impregnated with a metal salt.

8. The catalyst of claim 7 wherein said metal salt is a metal halide.

9. The catalyst of claim 8 wherein said metal halide is selected from the group consisting of cobalt, nickel, manganese, rhodium and ruthenium halide.

10. The catalyst of claim 9 wherein said halide is chloride.

11. The catalyst of claim 9 wherein said metal halide is cobalt chloride.

12. The catalyst of claim 7 wherein the loading of the metal salt is from about 0.1 to about 20 weight percent of the mixed oxide support.

13. The catalyst of claim 2 wherein said catalyst is from 5-90 percent fluorinated.

14. The catalyst of claim 1 wherein said catalyst is from 5-90 percent fluorinated.

* * * * *